US011753376B2

(12) United States Patent
Kwon et al.

(10) Patent No.: US 11,753,376 B2
(45) Date of Patent: Sep. 12, 2023

(54) BENZYLOXY PYRIDINE DERIVATIVES AND USES THEREOF

(71) Applicants: AUTOTAC INC., Seoul (KR); SEOUL NATIONAL UNIVERSITY R&DB FOUNDATION, Seoul (KR)

(72) Inventors: Yong Tae Kwon, Seoul (KR); Hyun Tae Kim, Seoul (KR); Jeong Eun Na, Seoul (KR); Chang Hoon Ji, Seoul (KR); Chang An Jung, Seoul (KR)

(73) Assignees: AUTOTAC INC., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 17/698,384

(22) Filed: Mar. 18, 2022

(65) Prior Publication Data
US 2022/0298113 A1 Sep. 22, 2022

(30) Foreign Application Priority Data
Mar. 19, 2021 (KR) .................. 10-2021-0035901

(51) Int. Cl.
C07D 213/69 (2006.01)
(52) U.S. Cl.
CPC .................. *C07D 213/69* (2013.01)
(58) Field of Classification Search
CPC .................................................... C07D 213/69
See application file for complete search history.

(56) References Cited

U.S. PATENT DOCUMENTS

| | | | |
|---|---|---|---|
| 2015/0175541 A1 | 6/2015 | Takayama et al. | |
| 2015/0175607 A1 | 6/2015 | Xie et al. | |
| 2018/0243244 A1 | 8/2018 | Kwon et al. | |
| 2022/0323379 A1* | 10/2022 | Kwon | A61P 25/28 |

FOREIGN PATENT DOCUMENTS

| | | |
|---|---|---|
| KR | 10-2015-0036219 A1 | 4/2015 |
| KR | 10-2017-0021525 A | 2/2017 |
| WO | 2004/004720 A1 | 1/2004 |
| WO | 2005/002673 A1 | 1/2005 |
| WO | 2012/064631 A1 | 5/2012 |
| WO | 2013/022919 A1 | 2/2013 |
| WO | 2016/200827 A1 | 12/2016 |

OTHER PUBLICATIONS

Shashikanth M. Sriram et al., "The N-end rule pathway: emerging functions and molecular principles of substrate recognition", Nature Reviews, Molecular Cell Biology, Nov. 2011, pp. 735-747, vol. 12.
Shashikanth M Sriram et al., "The molecular principles of N-end rule recognition", Nature Structural & Molecular Biology, Oct. 2010, pp. 1164-1165, vol. 17, No. 10.
Chang Hwa Jung et al., "mTOR regulation of autophagy," FEBS Lett, Apr. 2, 2010, pp. 1287-1295, vol. 584, No. 7.
Antonella Caccamo et al., "Molecular Interplay between Mammalian Target of Rapamycin (mTOR), Amyloid-β and Tau", The Journal of Biological Chemistry, Apr. 23, 2010, pp. 13107-13120, vol. 285, No. 17.
Jose A. Rodríguez-Navarro et al., "Trehalose ameliorates dopaminergic and tau pathology in parkin deleted/tau overexpressing mice through autophagy activation", Neurobiology of Disease, 2010, pp. 423-438, vol. 39.
Julie L. Webb et al., "α-Synuclein Is Degraded by Both Autophagy and the Proteasome", The Journal of Biological Chemistry, 2003, Issue of July 4, pp. 25009-25013, vol. 278, No. 27.
Brinda Ravikumar et al., "Aggregate-prone proteins with polyglutamine and polyalanine expansions are degraded by autophagy", Human Molecular Genetics, 2002, pp. 1107-1117, vol. 11, No. 9.
International Search Report for PCT/KR2020/012715, dated Dec. 23, 2020.
Xiaofang Lei et al., "In Situ Activation of Disulfides for Multicomponent Reactions with Isocyanides and a Broad Range of Nucleophiles", Organic Letters, 2019, vol. 21, pp. 1484-1487 (4 pages total).
Vince S.C. Yeh et al., "Practical Cu-catalyzed amination of functionalized heteroaryl halides", Tetrahedron Letters, 2006, vol. 47, pp. 6011-6016 (6 pages total).
Ho Yu Au-Yeung et al., "A selective reaction-based fluorescent probe for detecting cobalt in living cells", Chem. Commun., 2012, vol. 48, pp. 5268-5270 (3 pages total).
Communication dated Jul. 21, 2022 from the Korean Patent Office in Korean Application No. 10-2020-0121658.
Chang Hoon Ji et al., "Crosstalk and Interplay between the Ubiquitin-Proteasome System and Autophagy," Mol. Cells, 2017, pp. 441-449, vol. 40, No. 7.
Ivan Dikic et al., "Mechanism and medical implications of mammalian autophagy," Nature Reviews, Molecular Cell Biology, 2018, pp. 349-364, vol. 19.
Aaron Ciechanover et al., "Degradation of misfolded proteins in neurodegenerative diseases therapeutic targets and strategies", Experimental & Molecular Medicine, 2015, pp. 1-16, vol. 47, e147.
Takafumi Tasaki et al., "A Family of Mammalian E3 Ubiquitin Ligases That Contain the UBR Box Motif and Recognize N-Degrons", Molecular and Cellular Biology, Aug. 2005, pp. 7120-7136, vol. 25, No. 16.

* cited by examiner

*Primary Examiner* — D Margaret M Seaman
(74) *Attorney, Agent, or Firm* — Sughrue Mion, PLLC

(57) ABSTRACT

The present specification discloses a novel benzyloxy pyridine derivative compound represented by Chemical Formula 1, a salt thereof, a stereoisomer thereof, a hydrate thereof, or a solvate thereof, and novel uses thereof. The uses comprise the uses in the preparation of a composition for activating autophagy, a composition for activating p62 protein, a composition for inducing oligomerization of p62 protein, or a composition for ameliorating, preventing or treating a disease caused by misfolded protein.

8 Claims, 2 Drawing Sheets

BENZYLOXY PYRIDINE DERIVATIVES AND USES THEREOF

CROSS REFERENCE TO RELATED APPLICATION

The present application claims priority to Korean Patent Application No. 10-2021-0035901, filed Mar. 19, 2021, the entire contents of which is incorporated herein for all purposes by this reference.

BACKGROUND OF THE INVENTION

Field of the Invention

The present specification discloses a novel benzyloxy pyridine derivative compound and uses thereof.

Description of the Related Art

Autophagy is a protein degradation process essential to maintain cell homeostasis and genetic stability by degrading aged or impaired cellular organelles or damaged or abnormally folded proteins (Ji, C. H. & Kwon, Y. T., Mol Cells 40, 441-449 (2017)). In particular, when misfolded protein aggregates are accumulated in a cytoplasm, they can become cytotoxic substances, and thus, should be received and degraded by autophagy. The mechanism for autophagy is largely divided into macroautophagy, microautophagy and chaperone-mediated autophagy, and it is divided into bulk autophagy and selective autophagy, depending on the purpose of degrading the intracellular substrate (Dikic, I. & Elazar, Z., Nat Rev Mol Cell Biol 19, 349-364 (2018)).

Of these, selective autophagy and chaperone-mediated autophagy cause selective degradation of unwanted intracellular proteins and dysfunctional organelles. By inducing selective autophagy, the development of new therapies for diseases based on the accumulation of pathologically misfolded proteins and dysfunctional organelles is currently building a new paradigm. p62/SQSTM1/Sequestosome-1 protein is important for initiating the formation of autophagosome which is a mediator in the mechanism of selective autophagy, and delivering the contents. At this time, p62/SQRSM1/Sequestosome-1 bind to the misfolded proteins and their aggregates, which are delivered to autophagosome. P62 undergoes self-oligomerization as a key process when delivering misfolded proteins to autophagosomes (Ji, C. H & Kwon. Y. T., Mol Cells 40, 441-449 (2017)). At this time, the misfolded proteins are concentrated together to reduce the volume, thereby facilitating degradation by autophagy. PB1 domain mediates the self-oligomerization of p62, but the regulatory mechanism thereof is not well known. The misfolded protein-p62 conjugate delivered to autophagosome can be degraded by lysosomal enzymes as the autophagosome binds to a lysosome. Through the mechanism described above, autophagy is important for maintaining cell homeostasis by regulating intracellular changes in damaged proteins and cellular organelles. When autophagic function is weakened, it leads to the accumulation and aggregation of the misfolded proteins, which results in proteinopathies (Ciechanover, A. & Kwon, Y. T., Exp Mol Med 47, e147 (2015)). A key technique of the present invention is to provide a method for effectively eliminating misfolded proteins or its aggregates, which cause proteinopathies. For this purpose, it is necessary to activate only selective autophagy without activating bulk autophagy that have a wide range of effects on various biological pathways.

SUMMARY OF THE INVENTION

In one aspect, an object of the present disclosure is to provide a novel compound.

In one aspect, an object of the present disclosure is to provide a novel benzyloxy pyridine derivative compound, a salt thereof, a stereoisomer thereof, a hydrate thereof, or a solvate thereof.

In one aspect, an object of the present disclosure is to provide an autophagy activator.

In one aspect, an object of the present disclosure is to provide a p62 activator.

In one aspect, an object of the present disclosure is to induce oligomerization of p62 protein.

In one aspect, an object of the present disclosure is to eliminate in vivo misfolded protein.

In one aspect, an object of the present disclosure is to ameliorate, prevent or treat a disease caused by misfolded protein.

In one aspect, a compound according to the present disclosure is a compound having the structure of Chemical Formula 1 below, a salt thereof, a stereoisomer thereof, a hydrate thereof, or a solvate thereof:

[Chemical Formula 1]

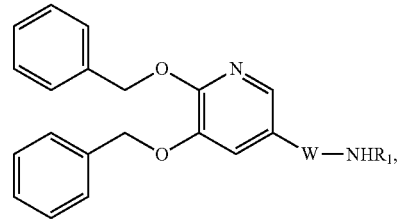

wherein W is a bond, —$(CH_2)n$ or —O—$(CH_2)$n-CH(OH)—$(CH_2)$n-, $R_1$ is —$(CH_2)nR_2$, $R_2$ is hydrogen, —OH, —$NH_2$, or —$COOCH_3$, and n is an integer from 0 to 6.

In one aspect, an autophagy activator composition according to the present disclosure comprises the above compound, a salt thereof, a stereoisomer thereof, a hydrate thereof, or a solvate thereof as an active ingredient.

In one aspect, a p62 protein activator composition according to the present disclosure comprises the above compound, a salt thereof, a stereoisomer thereof, a hydrate thereof, or a solvate thereof as an active ingredient.

In one aspect, a composition for inducing oligomerization of p62 protein according to the present disclosure comprises the above compound, a salt thereof, a stereoisomer thereof, a hydrate thereof, or a solvate thereof as an active ingredient.

In one aspect, a composition for ameliorating, preventing or treating proteinopathy according to the present disclosure comprises the above compound, a salt thereof, a stereoisomer thereof, a hydrate thereof, or a solvate thereof as an active ingredient.

In one aspect, a composition for eliminating in vivo misfolded protein according to the present disclosure comprises the above compound, a salt thereof, a stereoisomer thereof, a hydrate thereof, or a solvate thereof as an active ingredient.

In one aspect, a composition for ameliorating, preventing or treating a disease caused by misfolded protein according to the present disclosure comprises the above compound, a salt thereof, a stereoisomer thereof, a hydrate thereof, or a solvate thereof as an active ingredient.

In one aspect, the present disclosure may provide a novel benzyloxy pyridine derivative compound, a salt thereof, a stereoisomer thereof, a hydrate thereof, or a solvate thereof.

In one aspect, the present disclosure may activate autophagy.

In one aspect, the present disclosure may activate p62 protein.

In one aspect, the present disclosure may induce oligomerization of p62 protein.

In one aspect, the present disclosure may eliminate in vivo misfolded protein.

In one aspect, the present disclosure may ameliorate, prevent or treat a disease caused by misfolded protein.

DETAILED DESCRIPTION OF THE INVENTION

Figure 1:
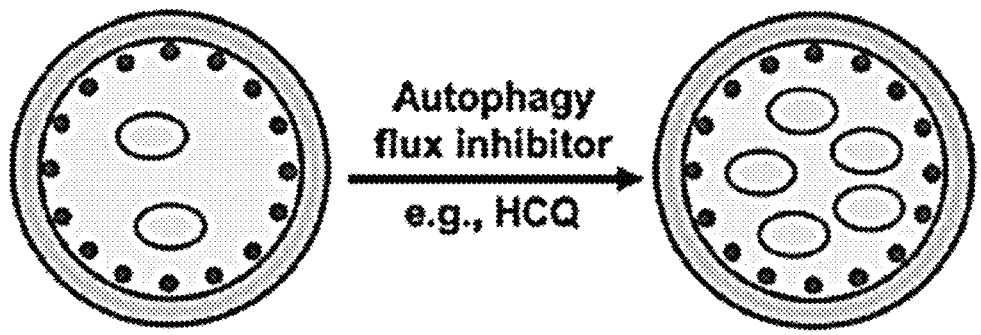
FIG. 1 is a schematic diagram showing a calculation method for measuring autophagy flux and an experimental background.

In one aspect, the present disclosure is directed to a compound having the structure of Chemical Formula 1 below, a salt thereof, a stereoisomer thereof, a hydrate thereof, or a solvate thereof:

[Chemical Formula 1]

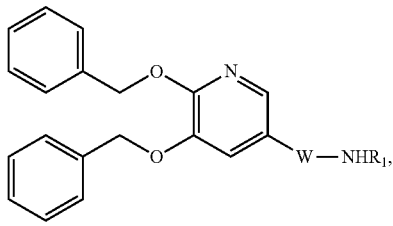

where W is a bond, —(CH$_2$)n or —O—(CH$_2$)n-CH(OH)—(CH$_2$)n-, R$_1$ is —(CH$_2$)nR$_2$, R$_2$ is hydrogen, —OH, —NH$_2$, or —COOCH$_3$, and n is an integer from 0 to 6.

In one embodiment, the above compound may be 2-(((5,6-bis(benzyloxy)pyridin-3-yl)methyl)amino)ethan-1-ol (ATB1110) or (R)-1-((5,6-bis(benzyloxy)pyridin-3-yl)oxy)-3-((2-hydroxyethyl)amino)propan-2-ol (ATB1116).

Meanwhile, the compound of the present disclosure may exist in the form of a pharmaceutically acceptable salt. As the salt, an acid addition salt formed by a pharmaceutically acceptable free acid is useful. The term "pharmaceutically acceptable salt" of the present disclosure refers to any and all organic or inorganic addition salts of the above compound in which adverse effect caused by the salt does not impair the beneficial effect of the compound according to the present disclosure at a concentration exhibiting relatively non-toxic and non-harmful effective activity to a patient. The acid addition salt is prepared by a common method, for example, by dissolving a compound in an excess amount of aqueous acid solution, and precipitating this salt using a water-miscible organic solvent such as methanol, ethanol, acetone or acetonitrile. An equimolar amount of a compound and an acid in water or alcohol (e.g., glycol monomethyl ether) can be heated, and subsequently, the resulting mixture can be dried by evaporating, or precipitated salts can be filtered under suction. In this case, the free acid may be an organic acid and an inorganic acid. The inorganic acid may comprise, but is not limited to, hydrochloric acid, phosphoric acid, sulfuric acid, nitric acid, tartaric acid, etc. The organic acid may comprise, but is not limited to, methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc. In addition, a pharmaceutically acceptable metal salt can be made using a base. An alkali metal salt or alkaline earth metal salt is obtained, for example, by dissolving a compound in an excess amount of alkali metal hydroxide or alkaline earth metal hydroxide solution, filtering the undissolved compound salt, and then evaporating the filtrate until dry. In this case, as the metal salt, it is particularly suitable for pharmaceutical use to prepare sodium, potassium, or calcium salt, but is not limited thereto. In addition, the corresponding silver salt can be obtained by reacting an alkali metal or alkaline earth metal salt with a proper silver salt (e.g., silver nitrate). The pharmaceutically acceptable salt of the compound of the present disclosure, unless otherwise indicated, comprises a salt of acidic or a basic group, which may be present in the compound represented by Chemical Formula 1 above. For example, the pharmaceutically acceptable salt may comprise sodium, calcium and potassium salt of hydroxy group, and other pharmaceutically acceptable salt of amino group, comprising hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salt, and the like. The salt may be prepared using a salt preparation method known in the art. The salt of the compound of Chemical Formula 1 of the present disclosure is a pharmaceutically acceptable salt, and can be used without particular limitation as long as it is a salt of the compound of Chemical Formula 1 which can exhibit a pharmacological activity equivalent to that of the compound of Chemical Formula 1, for example, can prevent or treat neurodegenerative diseases by inducing autophagic degradation of intracellular neurodegenerative disease and tumor-associated proteins through a ligand of p62. In addition, the compound represented by Chemical Formula 1 according to the present disclosure comprises, but is not limited thereto, not only a pharmaceutically acceptable salt thereof, but also a solvate such as a possible hydrate, and all possible stereoisomers that can be prepared therefrom. All stereoisomers of the present disclosure (e.g., those that may exist due to asymmetric carbons on various substituents), comprising enantiomeric form and diastereomeric form, are contemplated within the scope of the present disclosure. Individual stereoisomers of the compounds of the disclosure may be, for example, substantially free of other isomers (e.g., as a pure or substantially pure optical isomer having a certain activity), or, may be admixed, for example, as racemates or with all other, or other selected, stereoisomers. The chiral center of the compound of the present disclosure may have the S or R configuration as defined by the IUPAC 1974 Recommendations. The racemic form can be analyzed by physical methods, such as separation by chiral column chromatography, separation or crystallization of diastereomeric derivatives, or fractional shape crystallization. The individual optical isomers can be obtained from the racemates by any suitable method comprising, but not limited to, salt formation with an optically active acid followed by crystallization. The solvate and stereoisomer of the compound represented by Chemical Formula 1 may be prepared from the compound using methods known in the art. Furthermore, the compound represented by Chemical Formula 1 according to the present disclosure may be prepared in a crystalline form or in a non-crystalline form, and when prepared in a crystalline form, the compound may be optionally hydrated or solvated. In the present disclosure, the compound represented by Chemical Formula 1 may not only comprise a stoichiometric hydrate, but also comprise a compound containing various amounts of water. The solvate of the compound represented by Chemical Formula 1 according to the present disclosure comprises both a stoichiometric solvate and a non-stoichiometric solvate. In the preparation method of the present disclosure, as the reactants used in the above Reaction Schemes, commercially available compounds may be purchased and used as they are, or one or more reactions known in the art may be synthesized and used as they are or by appropriately being modified. For example, in consideration of the presence, type, and/or position of reactive functional groups and/or hetero elements contained in the skeletal structure, the reactants may be synthesized by performing one or more reactions in a series of order, but are not limited thereto.

In one aspect, the present disclosure is directed to an autophagy activator composition comprising the above compound, a salt thereof, a stereoisomer thereof, a hydrate thereof, or a solvate thereof as an active ingredient.

In one aspect, the present disclosure is directed to a p62 protein activator composition comprising the above compound, a salt thereof, a stereoisomer thereof, a hydrate thereof, or a solvate thereof as an active ingredient.

In one aspect, the present disclosure is directed to a composition for inducing oligomerization of p62 protein comprising the above compound, a salt thereof, a stereoisomer thereof, a hydrate thereof, or a solvate thereof as an active ingredient.

The p62 protein is important for initiating the formation of autophagosome, which is a mediator in the mechanism for selective autophagy, and delivering the contents. It was observed that significant p62 activation of the novel p62 ligand according to the present disclosure induces p62 self-oligomerization. In addition, in light of the fact that autophagosome targeting of p62 through such self-oligomerization is increased, this demonstrates that the novel p62 ligands according to the present disclosure can induce the targeting and degradation of p62 protein by intracellular autophagy. These results mean that the novel p62 ligand compounds according to the present disclosure can be used as a more effective or supplemental alternative to existing anti-protein disease drugs.

In one aspect, the present disclosure is directed to a composition for ameliorating, preventing or treating proteinopathy comprising the above compound, a salt thereof, a stereoisomer thereof, a hydrate thereof, or a solvate thereof as an active ingredient.

In one aspect, the present disclosure is directed to a composition for eliminating in vivo misfolded protein comprising the above compound, a salt thereof, a stereoisomer thereof, a hydrate thereof, or a solvate thereof as an active ingredient.

Such protein may be a main protein of proteinopathies, more preferably, one or more selected from the group consisting of pion protein, amyloid precursor protein (APP), alpha-synuclein, superoxide dismutase 1, tau, immunoglobulin, amyloid-A, transtyretin, beta 2-microglobulin, cystatin C, Apolipoproteine A1, TDP-43, islet amyloid polypeptide, ANF, gelsolin, insulin, lysozyme, fibrinogen, huntingtin, alpha-1-antitrypsin Z, crystallin, c9 open reading frame 72 (c9orf72), glial fibrillary acidic protein, cystic fibrosis transmembrane conductance regulator protein, rhodopsin and ataxin, and other proteins having Poly-Q stretch.

The term "proteinopathy" or "disease linked to protein aggregation" as used herein, refers to those diseases which are characterized by the presence of aggregated proteins. Examples thereof comprise, but are not limited to, neurodegenerative diseases, anti-alpha-1 antitrypsin deficiency, keratopathy, retinitis pigmentosa, type 2 diabetes, and cystic fibrosis. The neurodegenerative disease herein is preferably selected from the group consisting of Lyme borreliosis, Fatal familial insomnia, Creutzfeldt-Jakob Disease (CJD), multiple sclerosis (MS), dementia, Alzheimer disease, epilepsy, Parkinson's disease, stroke, Huntington's disease, Picks disease, amyotrophic lateral sclerosis (ALS), spinocerebellar ataxia, other poly-Q diseases, hereditary cerebral amyloid angiopathy, familial amyloid polyneuropathy, primary systemic amyloidosis (AL amyloidosis), reactive systemic amyloidosis (AA amyloidosis), injection-localized amyloidosis, beta-2 microglobulin amyloidosis, hereditary non-neuropathic amyloidosis, Alexander disease and Finnish hereditary systemic amyloidosis.

In one aspect, the present disclosure is directed to a method for activating autophagy, a method for activating p62 protein, a method for inducing oligomerization of p62 protein, or a method for ameliorating, preventing or treating a disease caused by misfolded protein, comprising administering an effective amount of a novel benzyloxy pyridine derivative compound according to Chemical Formula 1, a salt thereof, a stereoisomer thereof, a hydrate thereof, or a solvate thereof to a subject in need thereof.

In one aspect, the present disclosure is directed to a novel use of a novel benzyloxy pyridine derivative compound according to Chemical Formula 1, a salt thereof, a stereoisomer thereof, a hydrate thereof, or a solvate thereof, for the preparation of a composition for activating autophagy, a composition for activating p62 protein, a composition for inducing oligomerization of p62 protein, or a composition for ameliorating, preventing or treating a disease caused by misfolded protein.

The dosage of the pharmaceutical composition of the present disclosure may vary with a broad range depending on the weight, age, gender, health condition of a patient, diet, administration period, administration method, excretion rate, and severity of disease. However, it can be administered in a dosage of 0.1 ng/kg/day to 100 g/kg/day.

In addition, the present specification provides a technology for eliminating misfolded protein aggregates, which are a causative factor of degenerative brain diseases, by activating p62 which delivers the misfolded protein aggregates directly to autophagosome.

The composition of the present disclosure may further comprise a pharmaceutically acceptable carrier, diluents or excipients. The composition can be used in the various forms such as oral dosage forms of powders, granules, tablets, capsules, suspensions, emulsions, syrups, and aerosols, and injections of a sterile injectable solutions, which are formulated by the conventional method according to the purpose of each of the intended use. The composition can be administered through various routes comprising oral administration or intravenous, intraperitoneal, subcutaneous, rectal, and topical administration. Examples of suitable carriers, excipients or diluents which can be comprised in such compositions may comprise lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methyl hydroxy benzoate, propylhydroxy benzoate, talc, magnesium stearate, mineral oil, and the like. In addition, the composition of the present disclosure may further comprise fillers, anti-coagulants, lubricants, humectants, fragrances, emulsifiers, preservatives, and the like. A solid formulation for oral administration comprises tablets, pills, powders, granules, capsules, and the like, and such solid formulation is formulated by mixing the composition with one or more excipients, such as starch, calcium carbonate, sucrose, lactose, gelatin, and the like. In addition, lubricants such as magnesium stearate and talc may be used in addition to simple excipients. A liquid formulation for oral administration can be illustrated as suspensions, solutions, emulsions, syrups, and the like, and can comprise various excipients, such as humectants, sweeteners, fragrances, preservatives and the like, in addition to water and liquid paraffin, which are commonly used simple diluents. A formation for parenteral administration comprises sterilized aqueous solutions, non-aqueous solutions, suspension agents, emulsion agents, lyophilizing agents, and suppository agents. Non-aqueous solvent and suspending agent may comprise propylene glycol, polyethylene glycol, vegetable oil such as olive oil, and injectable esters such as ethyl oleate. As a substrate for the suppository agent, Withepsol, Macrogol, Tween61, Cacao butter, laurin paper, glycerogelatin, and the like can be used. Meanwhile, the injections may comprise conventional additives such as solubilizing agents, isotonic agents, suspending agents, emulsifiers, stabilizers, or preservatives. The formulation may be prepared by a conventional mixing, granulating or coating method, and contains an active ingredient in an amount effective for medical treatment, specifically preventing, ameliorating or treating diseases linked to misfolded protein aggregation. In this case, the composition of the present disclosure is administered in a pharmaceutically effective amount. The term "pharmaceutically effective amount" of the present disclosure refers to an amount which is sufficient to treat a disease at a reasonable benefit/risk ratio applicable to any medical treatment, and also which is enough to not cause side effects. The level of effective amount can be determined depending on patient's health condition, disease type, severity of the disease, activity of the drug, sensitivity on the drug, administration method, administration time, administration route, excretion rate, treatment duration, combination, factors comprising other medicines used at the same time and other factors well-known in the medical field. The composition of the present disclosure may be administered as an individual therapeutic agent or in combination with other therapeutic agents, and it may be administered sequentially or simultaneously with a conventional therapeutic agent, and once or multiple times. It is important to administer the minimum amount which can provide the maximum effect without side effects in consideration of all the above factors, which can be easily determined by a person skilled in the art. For example, the dosage may be increased or decreased depending on administration route, the severity of a disease, gender, weight, age, and the like, and the scope of the present disclosure is not limited by the aforementioned dosage in any way. A preferred dose of the compound according to the present disclosure may be varied according to the condition and weight of a patient, the severity of a disease, the type of a drug, and the route and duration of administration, but it may be appropriately selected by a person skilled in the art. In still another aspect, the present disclosure provides a method for increasing the degradation of misfolded protein aggregates, a method for activating autophagy, or a method for preventing, ameliorating or treating proteinopathy, comprising administering a p62 ligand compound of Chemical Formula 1 of the present disclosure, or a pharmaceutical composition comprising the same to a subject in need thereof. The term "subject" as used herein refers to all animals comprising human, monkeys, cows, horses, sheep, pigs, chickens, turkeys, quail, cat, dog, mouse, rat, rabbit, or guinea pig, which have the potential of metastasis and invasion of cancer, or cancer already metastasized and invaded, or have diseases linked to misfolded protein aggregation. The diseases linked to misfolded protein aggregation can be effectively prevented, ameliorated or treated by administrating the pharmaceutical composition of the present disclosure to the subject. In addition, since the pharmaceutical composition of the present disclosure functions as a p62 ligand to activate autophagy, eliminates aggregates of cancer-inducing proteins or misfolded proteins due to the autophagy activation, and thus exhibits a prophylactic or therapeutic effect of diseases linked to these aggregated proteins, it can exhibit synergistic effects by administration in combination with existing therapeutic agent. The term "administration" of the present disclosure refers to introduction of a predetermined substance to a patient in certain appropriate method, and the route of administration of the composition of the present disclosure can be administered through any general route as long as it can reach a target tissue. Intraperitoneal administration, intravenous administration, intramuscular administration, subcutaneous administration, intradermal administration, oral administration, topical administration, intranasal administration, intrapulmonary administration, and intrarectal administration, but the route is not limited thereto. In addition, the pharmaceutical composition of the present disclosure may be administered using any device capable of delivering the active ingredients to target cells. Preferred administration modes and formulations are an intravenous injection, a subcutaneous injection, an intradermal injection, an intramuscular injection, drip injections, and the like. Injectable formulations may be prepared using aqueous solutions such as saline. Ringer's solution, and non-aqueous solutions, such as vegetable oils, high fatty acid esters (e.g., ethyl oleic acid, etc.), alcohols (e.g., ethanol, benzyl alcohol, propylene glycol, glycerin, etc.). The injectable formulations may comprise pharmaceutical carriers such as stabilizer for preventing deterioration (e.g., ascorbic acid, sodium hydrogen sulfite, sodium pyrosulfite. BHA, tocopherol, EDTA, etc.), an emulsifier, a buffering agent for pH control, and a preservative for inhibiting microbial growth (e.g., phenylmercuric nitrate, thimerosal, benzalkonium chloride, phenol, cresol, benzyl alcohol, etc.). In still another aspect, the present disclosure provides a food composition for preventing or ameliorating proteinopathy comprising a p62 ligand compound of Chemical Formula 1, a pharmaceutically acceptable salt, stereoisomer, hydrate, solvate, or prodrug thereof. The food composition is a health functional food and it can be used through formulation itself, or be comprised in other health functional foods as an additive of health functional food. The health functional food refers to a food that has body modulating function such as preventing or ameliorating disease, biodefense, immunity, recovery of convalescence, aging inhibition, etc., and it should be harmless to human body when taking in a long time. The mixing amount of active ingredients may be appropriately decided depending on purpose of use (prevention, health or therapeutic treatment). There is no particular limitation on the type of the food. Examples of foods to which the above substances can be added comprise meat, sausage, bread, chocolate, candy, snacks, snack foods, pizza, ramen, other noodles, chewing gum, dairy products comprising ice cream, various soups, beverages, tea, health drinks, alcoholic beverages and vitamin complexes, and all health functional foods in the common sense. The food composition of the present disclosure may comprise common ingredients used in the preparation of food or food additives, specifically, a flavoring agent; a natural sweetener such as, monosaccharides like glucose and fructose, disaccharides like as maltose and sucrose, and dextrin, cyclodextrin as a natural carbohydrate, or a synthetic sweetener such as saccharin and aspartame; a nutrient; vitamin; electrolyte; a coloring agent; an organic acid; a protective colloid viscosity agent; pH regulator; a stabilizer; a preservative; glycerin; alcohol; a carbonating agent used in carbonated drinks, etc.

Hereinafter, the present disclosure is described with reference to examples, but this is only an example, and it is clear that the present disclosure is not intended to limit the scope of the present disclosure.

Example 1. Preparation of ATB1110 (2-(((5,6-bis (benzyloxy)pyridin-3-yl)methyl)amino)ethan-1-ol)

[Reaction Scheme 1]

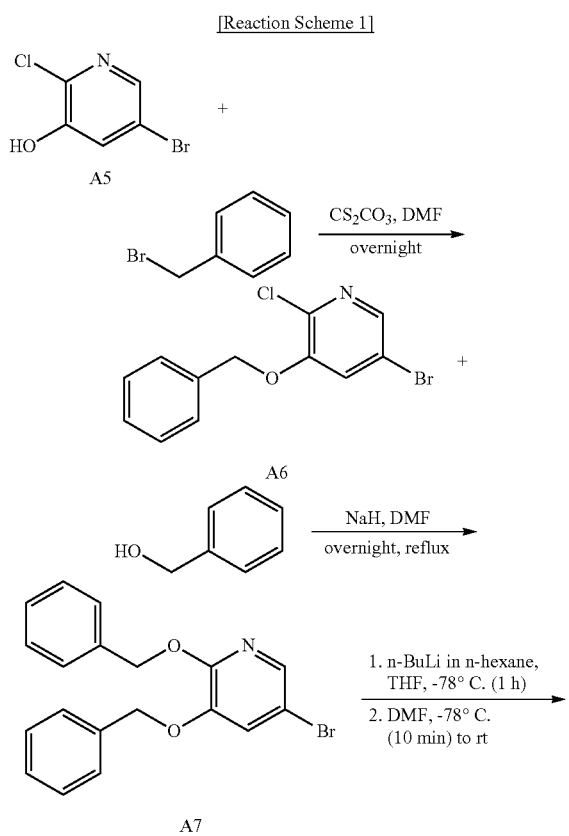

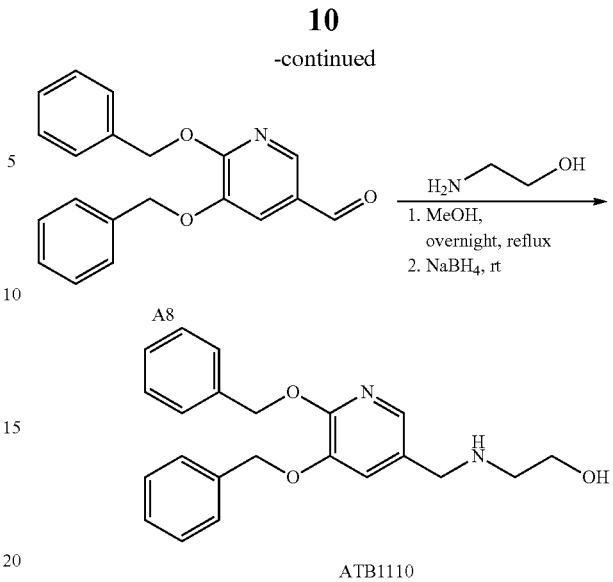

Step 1) Synthesis of A6

A mixture of 5-bromo-2-chloropyridine-3-ol (A5, 5.0 g, 2.40 mmol) and cesium carbonate ($Cs_2CO_3$, 12.0 g, 36.820 mmol) in dimethylformamide (DMF, 50 mL) was stirred at 0° C. To this stirred mixture was added benzyl bromide (3.40 ml, 28.57 mmol), slowly. The resulting solution was stirred at room temperature for 12 h. The mixture was diluted in ethyl acetate (EA). The organic layer was washed with distilled water, dried over $Na_2SO_4$, concentrated under reduced pressure to afford compound A6 (7.02 g) in 98.0% yield. ESI MS(m/e)=340 [M+$CH_3CN$+H]$^+$.

Step 2) Synthesis of A7

To a solution of benzyl alcohol (4.39 mL, 42.3 mmol) in dimethylformamide (DMF) were added sodium hydride (NaH, 1.52 g, 63.31 mmol) at 0° C., slowly. After 30 min, a compound A6 was added to the reaction mixture. The reaction flask was fitted with a reflux condenser, heated to 90° C., and stirred overnight. After completion, the reaction mixture was cooled room temperature and extracted with EA. The organic layer was washed with distilled water, dried over $Na_2SO_4$, and concentrated under reduced pressure, and purified by MPLC to afford compound A7 (2.41 g) in 24.6% yield. ESI MS(m/e)=371 [M+H]$^+$ Step 3) Synthesis of A8

A mixture of A7 (1.0 g, 5.40 mmol) in tetrahydrofuran (THF, 12.3 mL, 151.2 mmol) was stirred at −78° C. under argon. After 30 min, n-butyl lithium (n-BuLi, 2.6 mL, 27.7 mmol) was added to the reaction at −78° C. for 1 h. And then, dimethylformamide (DMF, 0.9 mL, 11.3 mmol) was added to the reaction for 40 min. After completion, the reaction mixture was quenched with saturated aqueous $NH_4Cl$. And then, the resulting mixture was dissolved in ethyl acetate. The organic layer was washed with brine, dried over $Na_2SO_4$, concentrated under reduced pressure, and then purified by MPLC to afford compound A8 (0.13 g) in 14.7% yield. ESI MS(m/e)=320 [M+H]$^+$ Step 4) Synthesis of ATB1110 (2-(((5,6-bis(benzyloxy)pyridin-3-yl)methyl)amino)ethan-1-ol)

A mixture of A8 (0.13 g, 0.40 mmol) and 2-aminoethanol (0.02 mL, 0.40 mmol) in methanol (5 mL) were stirred at 70° C. for 12 h, equipped with a refluxing condenser. Then, $NaBH_4$ (0.02 g, 0.40 mmol) was added to the reaction at cool temperature. The mixture was stirred at room temperature for 4 h. Then the mixture was dissolved in dichloromethane (DCM). The organic layer was washed with distilled water, dried over $Na_2SO_4$, concentrated under reduced pressure, and purified by MPLC to afford 2-(((5,6-bis(benzyloxy)pyridin-3-yl)methyl)amino)ethan-1-ol (ATB1110, 0.07 g) in 51.7% yield. $^1$H NMR (DMSO_$d_6$, 600 MHz): δ 7.63 (d, J=1.5 Hz, 1H), 7.46-7.42 (m, 5H), 7.40-7.28 (m, 6H), 5.38 (s, 2H), 5.13 (s, 2H), 4.51 (s, 1H), 3.65 (s, 2H), 3.45 (t, J=5.7 Hz, 2H), 2.54 (t, J=5.8 Hz, 2H), ESI MS(m/e)=363 [M+H]$^+$ Example 2. Preparation of ATB1116 ((R)-1-((5,6-bis(benzyloxy)pyridin-3-yl)oxy)-3-((2-hydroxyethyl)amino)propan-2-ol)

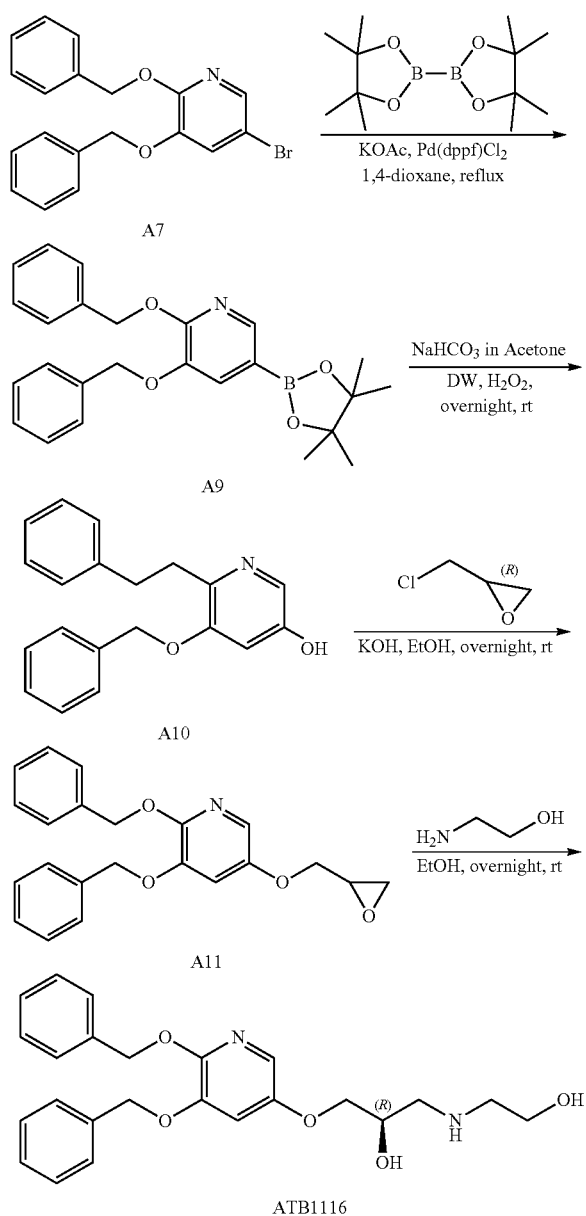

[Reaction Scheme 2]

Step 1) Synthesis of A9
A mixture of A7 (0.46 g, 1.24 mmol), pinacol boron (0.38 g, 1.4 mmol), potassium acetate (KOAc, 0.33 g, 3.1 mmol) and Pd(dppf)Cl$_2$ in 1,4-dioxane (11.4 mL) were stirred at 100° C. for 5 h, equipped with a refluxing condenser under argon. After cooling at room temperature, the mixture was diluted with dichloromethane (DCM). The organic layer was washed with distilled water, dried over $Na_2SO_4$, concentrated under reduced pressure and purified by MPLC to afford compound A9 (0.25 g) in 48.6% yield. ESI MS(m/e)=418 [M+H]$^+$ Step 2) Synthesis of A10
A mixture of A9 (0.25 g, 0.61 mmol), $NaHCO_3$ (0.36 g, 4.2 mmol), distilled water (1.1 mL, 59.7 mmol) and $H_2O_2$ (0.05 mL, 1.8 mmol) in acetone were stirred at room temperature for 12 h. After completion, the reaction mixture was quenched with saturated aqueous $NaHCO_3$. And then, the resulting mixture was dissolved in dichloromethane. The organic layer was washed with brine, dried over $Na_2SO_4$, concentrated under reduced pressure, and purified by MPLC to afford compound A10 (0.15 g) in 81% yield. ESI MS(m/e)=308 [M+H]$^+$ Step 3) Synthesis of A11
A mixture of A10 (0.15 g, 0.49 mmol), potassium hydroxide (KOH, 0.03 g, 0.59 mmol), (R)-Epichlorohydrin (0.19 mL, 2.44 mmol) in ethanol (10 mL) were stirred at room temperature for 12 h. After completion, the reaction mixture was diluted with dichloromethane (DCM). The organic layer was washed with distilled water, dried over $Na_2SO_4$, concentrated under reduced pressure and purified by MPLC to afford compound A11 (0.08 g) in 42.8% yield. ESI MS(m/e)=364 [M+H]$^+$ Step 4) Synthesis of ATB1116 ((R)-1-((5,6-bis(benzyloxy)pyridin-3-yl)oxy)-3-((2-hydroxyethyl)amino)propan-2-ol)

A mixture of A11 (0.0759 g, 0.21 mmol), 2-aminoethanol (0.63 ml, 1.04 mmol) in ethanol (5 mL) were stirred at room temperature for 12 h. The mixture was concentrated under reduced pressure and purified by MPLC to afford (R)-1-((5,6-bis(benzyloxy)pyridin-3-yl)oxy)-3-((2-hydroxyethyl)amino)propan-2-ol (ATB1116, 0.05 g) in 51.1% yield. $^1$H-NMR (500 MHz, DMSO-d$_6$) δ 7.44-7.40 (m, 5H), 7.39-7.37 (m, 3H), 7.36-7.32 (m, 2H), 7.31-7.28 (m, 1H), 7.10 (d, J=2.6 Hz, 1H), 5.33 (s, 2H), 5.16 (s, 2H), 4.99 (s, 1H), 4.49 (t, J=5.2 Hz, 1H), 3.93 (dd, J=9.3, 4.2 Hz, 1H), 3.87-3.80 (m, 2H), 3.46-3.43 (m, 2H), 2.66-2.55 (m, 4H), ESI MS(m/e)= 479 [M+CH$_3$OH+Na]$^+$

[Experimental Example 1] Evaluation of Intracellular Autophagy Activity by Immunoblotting In order to evaluate the autophagy flux activity efficacy by the compounds, the HEK293T cell line, which is a cell line derived from a human embryonic kidney-derived cell, was cultured using a DMEM medium containing 10% FBS and 1% streptomycin/penicillin in an incubator with 5% carbon dioxide. In order to measure the autophagy flux activity according to the treatment of the compounds synthesized in the above examples, each cell was dispensed in a 6-well plate. Additional incubation was carried out for 24 hours so that the cells were completely attached to the surface of the plate. Cells were collected after treatment with the compound (5 μM) alone or with the lysosomal inhibitor, hydroxychloroquine (HCQ) (5 μM) for 24 hours to determine whether the compound increases autophagy flux. To extract proteins from the collected cells, 100 μL of lysis buffer (20 mM Tris, pH 7.4, 150 mM NaCl, 1% triton-X-100, 2 mM NaF, 2 mM EDTA, 2 mM b-glycerophosphate, 5 mM sodium orthovanadate, 1 mM PMSF, leupeptin, aprotenin) were injected in each sample and the cells were lysed. Based on the measured total protein concentration, a sample buffer was added to each sample and reacted at 100° C. for 5 minutes. After completing the reaction, 5 μL was taken from the samples and dispensed into each well of acrylamide gel, and then immunoblotting was performed. The experimental background is shown in FIG. 1 and the result is shown in FIG. 2.

FIG. 1 is a schematic diagram showing a calculation method for measuring autophagy flux and an experimental background.

Figure 2:
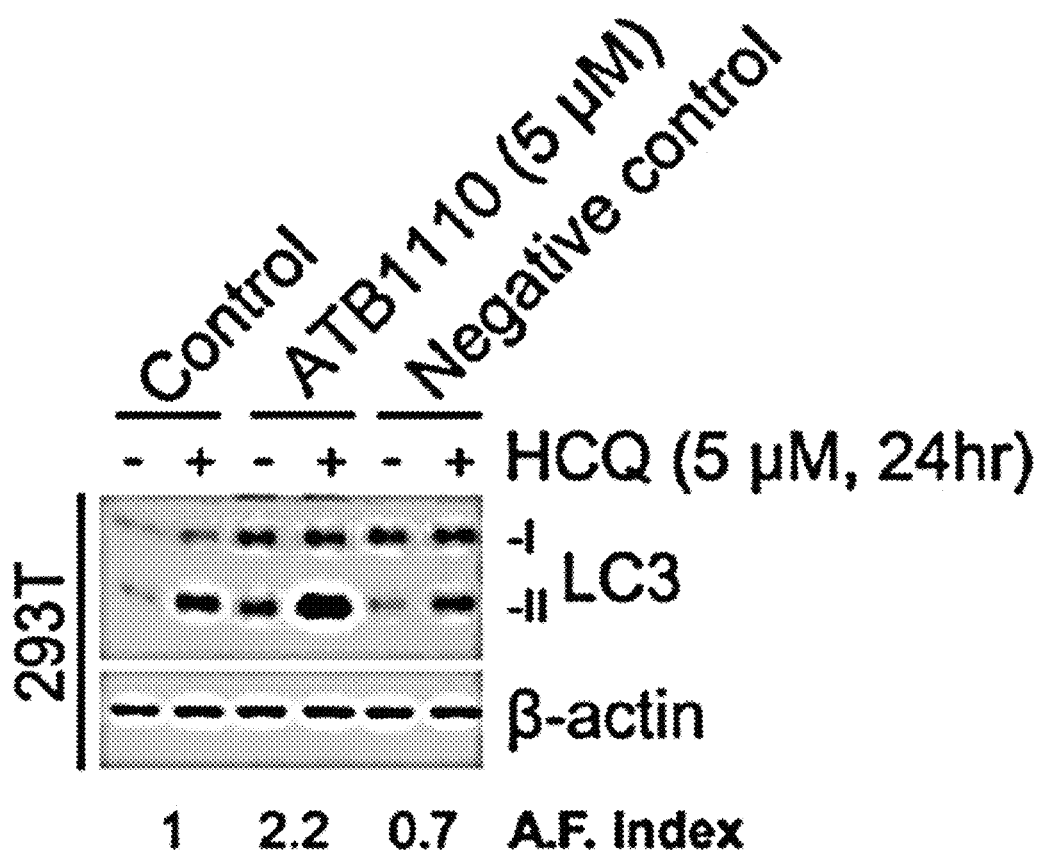
FIG. 2 is a result of immunoblotting showing the efficacy of compounds of one embodiment of the present disclosure to activate intracellular autophagy flux.

FIG. 2 is a result of immunoblotting showing the efficacy of the compound (ATB1110) to activate intracellular autophagy flux. The compound was treated either alone or in combination with a lysosomal inhibitor, hydroxychloroquine (HCQ). As HCQ was treated, the level of LC3-II, a marker of autophagy activity, was increased, and the difference between LC3-II in the untreated state and the treated state was measured. It indicates that the difference value of LC3-II is further increased in the case that was treated with ATB1110, compared to the case of a Control that was not treated with any compound or a DMSO negative control that did not affect the autophagy flux. This result was quantified. The immunoblotting showed representative results from three or more independent experiments.

LC3-II protein is a target protein eliminated by autophagy, and a high level indicates low autophagy activity. When HCQ, a lysosomal inhibitor, is treated, autophagy activity is lowered and thus LC3-II level is increased. However, when the compound of the above example was treated together, the increased level of LC3-II by HCQ was significantly lowered. The lowering degree is significantly larger when treated with the compound of the above example, compared to the lowering degree in Control or Negative control. A.F, index value derived according to the formula of FIG. 1. indicates the lowering degree, and as illustrated in the lower part of FIG. 2, it can be seen that the value of ATB1110, the compound according to the above example, is the highest compared to the value of Control or Negative control. This indicates the autophagy activation efficacy of ATB1110.

[Experimental Example 2] Evaluation of p62 Protein Oligomers and Activity in Cultured Cells by Immunoblotting In order to evaluate the oligomerization activity efficacy of the p62 protein of the compounds synthesized in the above example, a HEK293 cell line, which is a cell line derived from a human embryonic kidney-derived cell, was dispensed in 100 pie dishes, and the cells were collected after additional incubation for 24 hours so that the cells were completely attached to the surface of the plate. 100 μl of lysis buffer (20 mM Tris (pH 7.4), 150 mM NaCl, 1% Triton X-100, 2 mM NaF, 2 mM EDTA, 2 mM beta-glycerophosphate, 5 mM sodium orthovanadate, 1 mM PMSF, leupeptin, and aproteinin) was injected in the collected cells and the cells were lysed. Based on the measured total protein concentration, each sample was treated with 1 mM of the test compounds at room temperature for 2 hours, and then, a sample buffer was added and reacted at 95° C. for 10 minutes. 25 μl of the samples where reaction was completed were taken and dispensed into each well of acrylamide gel, and then immunoblotting was performed. The immunoblotting showed representative results from three or more independent experiments. The result is shown in FIG. 3.

Figure 3:
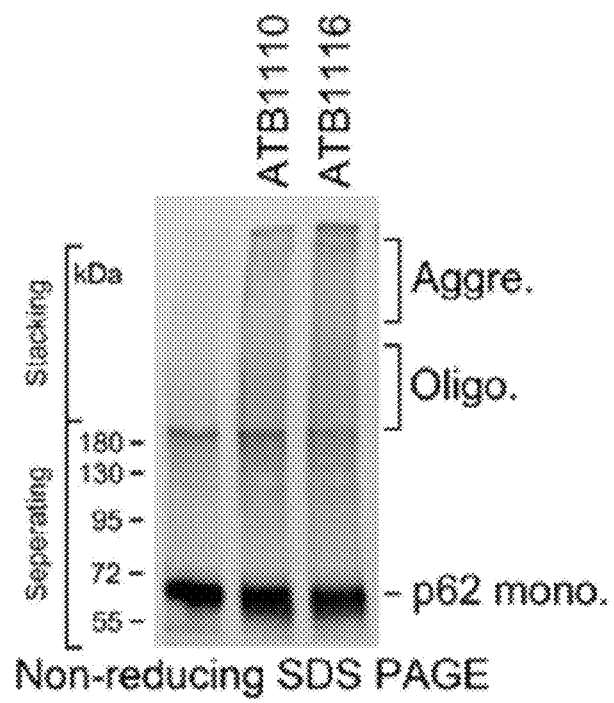
FIG. 3 is a result of immunoblotting showing the efficacy of the compounds of one embodiment of the present disclosure to structurally activate intracellular p62 protein.

As can be seen in FIG. 3, it can be confirmed that when the compound of the above example was treated, the oligomers and high-molecular aggregates of the p62 protein was increased according to the treatment of the compounds.

What is claimed is:

1. A compound of the following Chemical Formula 1, a salt thereof, a stereoisomer thereof, a hydrate thereof, or a solvate thereof:

[Chemical Formula 1]

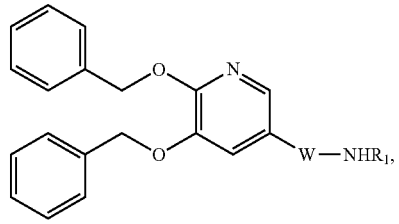

wherein W is a bond, —$(CH_2)n$ or —O—$(CH_2)n$-CH(OH)—$(CH_2)n$-, $R_1$ is —$(CH_2)nR_2$, $R_2$ is hydrogen or —OH, and n is an integer from 0 to 6.

2. The compound, a salt thereof, a stereoisomer thereof, a hydrate thereof, or a solvate thereof according to claim 1, wherein the compound of the Chemical Formula 1 is 2-(((5,6-bis(benzyloxy)pyridin-3-yl)methyl)amino)ethan-1-ol or (R)-1-((5,6-bis(benzyloxy)pyridin-3-yl)oxy)-3-((2-hydroxyethyl)amino)propan-2-ol.

3. A method for activating autophagy in a subject in need thereof, comprising administering to the subject an effective amount of the compound, a salt thereof, a stereoisomer thereof, a hydrate thereof, or a solvate thereof according to claim 1.

4. The method according to claim 3, wherein the compound is 2-(((5,6-bis(benzyloxy)pyridin-3-yl)methyl)amino)ethan-1-ol or (R)-1-((5,6-bis(benzyloxy)pyridin-3-yl)oxy)-3-((2-hydroxyethyl)amino)propan-2-ol.

5. The method according to claim 3, wherein the autophagy activation is caused by activation of p62 protein.

6. The method according to claim 3, wherein the autophagy activation is caused by inducing oligomerization of p62 protein.

7. The method according to claim 4, wherein the autophagy activation is caused by activation of p62 protein.

8. The method according to claim 4, wherein the autophagy activation is caused by inducing oligomerization of p62 protein.

* * * * *